United States Patent [19]

Watanabe et al.

[11] Patent Number: 4,487,924
[45] Date of Patent: Dec. 11, 1984

[54] 2'-N-(β-LYSYL) AMINOGLYCOSIDES

[75] Inventors: Isamu Watanabe; Kazuhiro Kamiya; Toshihito Mori, all of Higashimurayama, Japan

[73] Assignee: Kowa Company, Ltd., Nagoya, Japan

[21] Appl. No.: 494,556

[22] Filed: May 13, 1983

[30] Foreign Application Priority Data

May 14, 1982 [JP] Japan ................................. 57-80066

[51] Int. Cl.³ ............................................. C07H 15/22
[52] U.S. Cl. ................................... 536/16.1; 536/16.8
[58] Field of Search ............................. 536/16.1, 16.8

[56] References Cited

U.S. PATENT DOCUMENTS 4,216,210 8/1980 Carney et al. ..................... 336/16.1
4,330,673 5/1982 Rosenbrook, Jr. ................ 536/16.1
4,360,666 11/1982 Tadanier et al. .................. 536/16.1

*Primary Examiner*—Johnnie R. Brown
*Assistant Examiner*—Elli Peselev
*Attorney, Agent, or Firm*—Wenderoth, Lind & Ponack

[57] ABSTRACT

A compound of the following formula

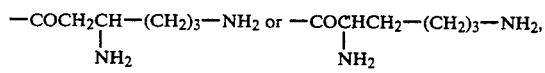

wherein each of $R_1$, $R_2$ and $R_3$ represents H or $CH_3$, $R_4$ represents H or $C_2$–$C_4$ acyl substituted at the 2-, 3- or 4-position by an amino group, and Y represents $$-COCH_2\underset{NH_2}{CH}-(CH_2)_3-NH_2 \text{ or } -CO\underset{NH_2}{CH}CH_2-(CH_2)_3-NH_2,$$

provided that $R_1$ and $R_2$ are not $CH_3$ at the same time, and an acid addition salt thereof; and a process for the production thereof.

4 Claims, No Drawings

2'-N-(β-LYSYL) AMINOGLYCOSIDES

This invention relates to novel aminoglycosides and a process for production thereof. The novel aminoglycosides are useful as antibiotics.

More specifically, this invention pertains to compounds represented by the following formula (I)

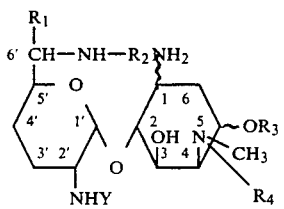

wherein each of $R_1$, $R_2$ and $R_3$ represent H or $CH_3$, $R_4$ represents H or $C_2$–$C_4$ acyl substituted at the 2-, 3- or 4-position by an amino group, and Y represents

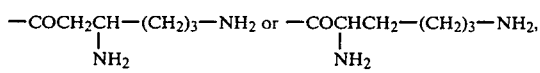

provided that $R_1$ and $R_2$ are not $CH_3$ at the same time, and acid addition salts thereof.

Aminoglycosides KA-6606 compounds, KA-7038 compounds and their 5-de-O-methyl derivatives of the following formula (II)'

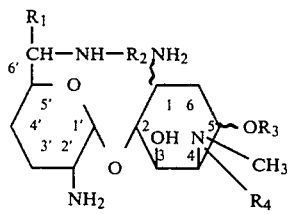

wherein $R_1$, $R_2$, $R_3$ and $R_4$ are as defined in formula (I), are known. KA-6606I to KA-6606 IV compounds are disclosed, for example, in West German OLS 2813021 (corresponding to U.S. Pat. No. 4,206,206); KA-6606V to KA-6606 VI compounds, in Japanese Laid-Open Patent Publication No. 111497/1980; KA-6606 VII to XVII compounds, in EPC Laid-Open Publication No. 44,477; and KA-6606 XVIII and XIX compounds, in Japanese Patent Application No. 11805/1982. KA-7038I to KA-7038 VII compounds are disclosed, for example, in West German OLS 2928373 (corresponding to U.S. Pat. No. 4,312,858); and KA-7038 VIII to KA-7038 XI compounds, in J. Chem. Soc., Jpn., Ind. Chem. 1982 (10) 1696. The 5-de-O-methyl derivatives of these KA-6606 and KA-7038 compounds are disclosed, for example, in West German OLS 2942194 (corresponding to U.S. Pat. No. 4,255,421).

The present inventors have made investigations about aminoglycosides having good antibiotic activity which are derived from the above-exemplified known aminoglycosides KA-6606 compounds, KA-7038 compounds and their 5-de-O-methyl derivatives.

As a result, they have discovered that novel aminoglycosides not described in the prior literature, which are represented by formula (I) given above wherein the hydrogen atom of the amino group at the 2'-position is replaced by a lysine or β-lysine residue, can exist. They have also succeeded in synthesizing these compounds.

It has also been found that the novel aminoglycosides of formula (I) can be produced easily in good yields by reacting the known aminoglycoside of formula (II)' or a compound of formula (II)' in which the amino groups other than the amino group at the 2'-position are protected with protective groups, with lysine or β-lysine in which the amino groups are protected by protective groups, or its reactive derivative, and then eliminating the protective groups.

They have further discovered that since the lysine or β-lysine in which the amino groups are protected or its reactive derivative has a great tendency to react selectively with the amino group at the 2'-position in the aforesaid reaction, it is not always necessary to protect the other amino groups with protective groups.

It has also been found that the resulting novel aminoglycosides of formula (I) have excellent antibiotic activity.

It is an object of this invention to provide novel aminoglycosides and a process for production thereof.

The above and other objects of this invention along with its advantages will become more apparent from the following description.

The novel aminoglycosides of formula (I) in accordance with this invention can be produced by reacting a compound of the following formula (II) in which the amino groups other than the amino-group at the 2'-position may be protected by protective groups,

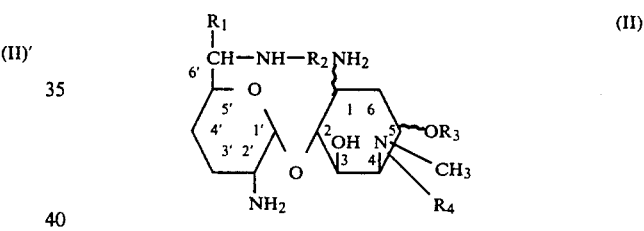

wherein each of $R_1$, $R_2$ and $R_3$ represent H or $CH_3$, and $R_4$ represents H or $C_2$–$C_4$ acyl substituted at the 2-, 3- or 4-position by an amino group, provided that $R_1$ and $R_2$ are not $CH_3$ at the same time, and the amino groups other than the amino group at the 2'-position may be protected by protective groups, with lysine or β-lysine in which the amino groups are protected by protective groups, or its reactive derivative, and thereafter eliminating the protective groups.

The known aminoglycosides KA-6606 compounds and KA-7038 compounds of formula (II)' above which are included within the above formula (II) and their 5-de-O-methyl derivatives are known from the above-cited literature references. Some compounds are exemplified below.

KA-6606 compounds and their 5-de-O—methyl derivatives:

KA-6606I

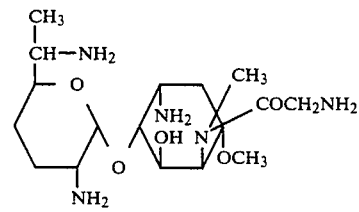

-continued
5-de-O—methyl-KA-6606I
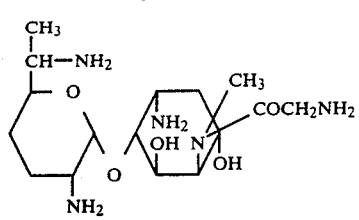
KA-6606II
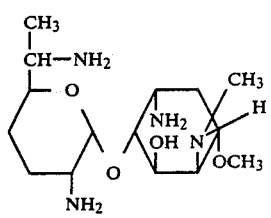
5-de-O—methyl-KA-6606II
(KA-6606XI)
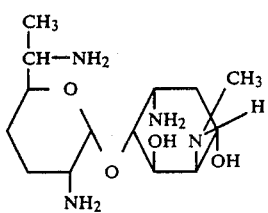
KA-6606VI
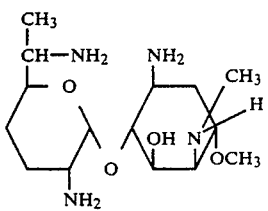
5-de-O—methyl-KA-6606VI
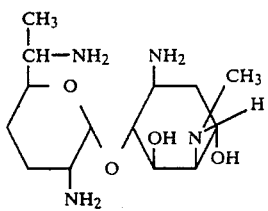
KA-6606VIII
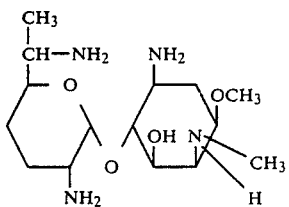
5-de-O—methyl-KA-6606VIII
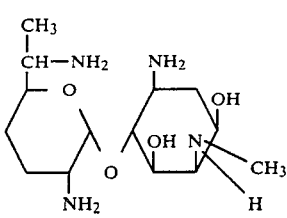
KA-6606XIV
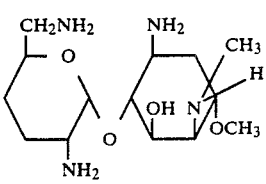
5-de-O—methyl-KA-6606XIV
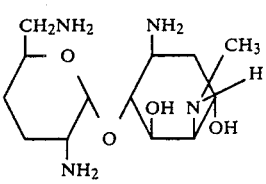
KA-6606XIX
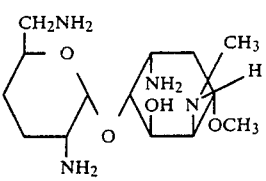
5-de-O—methyl-KA-6606XIX
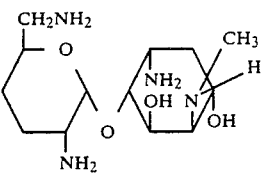
KA-7038 compounds and their 5-de-O—methyl derivatives:
KA-7038I
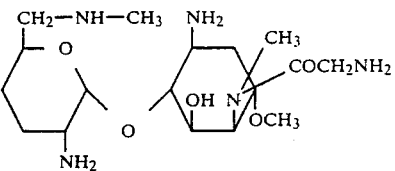
5-de-O—methyl-KA-7038I
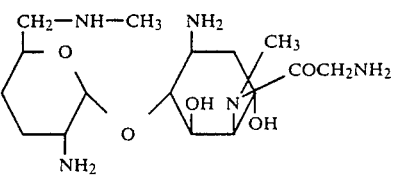

-continued

KA-7038III

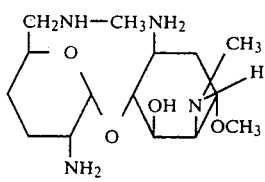

5-de-O—methyl-KA-7038III

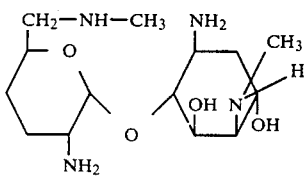

KA-7038VI

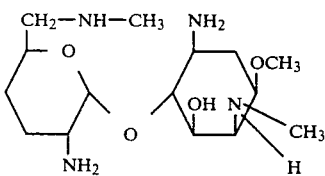

5-de-O—methyl-KA-7038VI

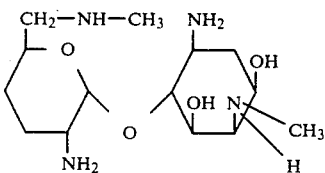

KA-7038IX

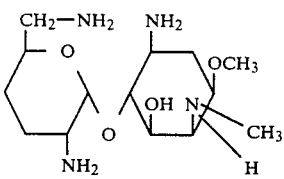

5-de-O—methyl-KA-7038IX

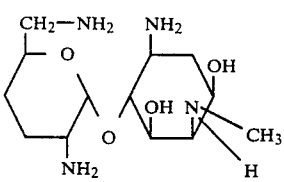

The compounds of formula (I) of this invention can be produced by reacting the compound of formula (II), which encompasses the compounds of formula (II)' and those of formula (II)' in which the amino groups other than the amino group at the 2'-position are protected by protective groups, with lysine

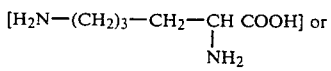

-continued

β-lysine [H$_2$N(CH$_2$)$_3$—CH—CH$_2$COOH]
$\quad\quad\quad\quad\quad\quad\quad\quad\quad$|
$\quad\quad\quad\quad\quad\quad\quad\quad\;$NH$_2$ or its reactive derivative in which the amino groups are protected by protective groups, and then eliminating the protective groups.

Since the lysine or β-lysine or its reactive derivative having the amino groups protected by protective groups has a great tendency to react selectively with the amino group at the 2'-position of the aminoglycoside of formula (II), it is not always necessary to protect the other amino groups of the compound (II) with protective groups (see, for example, Examples 1 to 3). However, when R$_1$ and R$_2$ in formula (II) are both hydrogen atoms or when R$_4$ is not a hydrogen atom, it is preferred to protect the other amino groups because it enables the reaction to be easily controlled. When in formula (II), the 1-position and/or the 4-position and/or the 6'-position and/or R$_4$ is an acyl group substituted by an amino group, such amino groups are the amino groups other than the amino group at the 2'-position of the compound of formula (II).

The protective groups for the other amino groups of the compound of formula (II) can be eliminated simultaneously with the deprotection of the protected amino groups of lysine, β-lysine or its reactive derivative after the compound of formula (II) has been reacted with lysine or its derivative. Hence, it is not necessary to deprotect the protected amino groups in a multiplicity of steps.

Protective groups for an amino group which are customarily used in peptide synthesis can, for example, be used as protective groups for the amino groups of the compound of formula (II) other than the amino group at the 2'-position and for the amino groups of lysine, β-lysine or its reactive derivative. Specific examples of the protective groups include C$_2$–C$_8$ alkyloxycarbonyl groups such as ethyloxycarbonyl, tertiary butyloxycarbonyl and tertiary amyloxycrbonyl; C$_5$–C$_8$ cycloalkyloxycarbonyl groups such as cyclohexyloxycarbonyl; a phenoxycarbonyl group; and a benzyloxycarbonyl group which may be substituted by a substituent selected from the class consisting of nitro, C$_1$–C$_3$ alkyl and C$_1$–C$_3$ alkoxy.

The amino groups of the compound of formula (II) other than the amino group at the 2'-position can be protected by techniques known per se. For example, when in formula (II) both R$_1$ and R$_2$ are hydrogen atoms or when R$_4$ is not a hydrogen atom, the amino group in the 6'-position or 4-position side chain can be protected by reacting the compound of formula (II) with one equivalent of an active ester of a protective group, such as benzyloxycarbonyloxysuccinimide, in water, methanol, ethanol, dioxane, tetrahydrofuran or a mixture of these with stirring at −20° C. to room temperature for 0.5 to 10 hours. When one of R$_1$ and R$_2$ is CH$_3$ or R$_4$ is hydrogen, the amino groups other than the amino group at the 2'-position can be protected as follows: The compound of formula (II) is reacted with one equivalent of an active ester of a protective group which can be eliminated by a different method (e.g., with an acid) from that used to eliminate the aforesaid protective group, such as S-p-methoxybenzyloxycarbonyl-4,6-dimethyl-2-mercaptopyrimidine, under the same conditions as above to obtain a 2'-protected product of the compound of formula (II). Preferably, the other amino groups are protected by the same protective groups as those used in protecting the amino groups in the 6'-position or 4-position side chain. A strong reagent such as carbobenzoxy chloride can also be used, and slightly more severe reaction conditions may be used. Finally, the protected compound of formula (II) is subjected to the action of an acid such as trifluoroacetic acid or p-toluenesulfonic acid at 0° C. to 40° C. to eliminate the 2'-position protective group and to obtain the protected compound of formula (II) in which only the amino group at the 2'-position is free.

The amino groups of lysine, β-lysine or its reactive derivative may be protected by techniques known per se. For example, the two amino groups can be protected without racemization by dissolving lysine or β-lysine in water containing one equivalent (2 equivalents in the case of a monohydrochloride) of an alkali such as sodium hydroxide, and adding 2 equivalents of an alkali and carbobenzoxychloride little by little at 0° C. to room temperature with stirring.

The reaction derivative of lysine or β-lysine may, for example, be an acid halide, acid azide, acid anhydride or active ester of such lysine. The active ester is preferred. Examples of the active ester are substituted phenyl esters such as p-nitrophenyl ester or 2,4-dinitrophenyl ester, and N-oxyimide esters such as N-oxysuccinimide ester or N-oxyphthalimide ester.

The compound of formula (I) in accordance with this invention can be produced by reacting the compound of formula (II) with lysine or β-lysine or its reactive derivative whose amino groups are protected by protective groups, and then eliminating the protective groups.

The reaction can be carried out by contacting the compound of formula (II) with the amino-protected lysine or β-lysine or its reactive derivative in a suitable solvent in the presence or absence of a divalent metal salt, preferably a divalent metal acetate, or an organic base, preferably a teritary amine. Examples of the solvent are alcohols such as methanol and ethanol; ethers such as dioxane and tetrahydrofuran; water; dimethylformamide; acetonitrile; halogenated hydrocarbons such as dichloromethane and chloroform; and mixtures of these. Examples of the divalent metal salt are nickel acetate, cobalt acetate, copper acetate and zinc acetate. Examples of the organic base are triethylamine, pyridine, collidine and 1,8-diazabicyclo(5,4,0)-7-undecene.

The reaction temperature can be suitably selected. For example, the reaction can be carried out at room temperature, or under cooling or heating (for instance, at a temperature of from about −10° C. to about 60° C.). The reaction time can also be suitably selected, and is, for example, about 1 to about 30 hours.

The free compound of formula (I) can be obtained by eliminating the protective groups of the resulting compound of formula (I) in which 1 to 5 amino groups are protected. Deprotection can be effected by techniques known per se, preferably by a catalytic reducing method and an acid decomposition method. The catalytic reduction can be carried out, for example, by reducing the product with hydrogen in a suitable solvent in the presence of a suitable reducing catalyst. The reducing catalyst is preferably one composed of a metal of Group VIII of the periodic table such as palladium, platinum, Raney nickel, rhodium, ruthenium and nickel. The solvent may be the same as those exemplified hereinabove. The reaction conditions can be properly selected. For example, the hydrogen pressure is about 1 to about 5 atmospheres, the reaction temperature is about 0° to about 100° C., and the reaction time is about 0.1 to about 10 hours.

The acid decomposition can be carried out by decomposing the product with a suitable acid in a suitable solvent. Examples of acids that can be used are hydrochloric acid, hydrobromic acid or hydrofluoric acid. Examples of the solvent are acetic acid, methanol, ethanol, dioxane, and water. The reaction conditions can be suitably selected. For example, the reaction temperature is 0° to 100° C., and the reaction time is 0.1 to 10 hours.

The compound of formula (I) so produced can be in the form of its acid addition salt, preferably its pharmaceutically acceptable acid addition salt. The acid addition salt can be obtained by contacting the compound of formula (I) in free form with a suitable acid in accordance with means known per se. The desired addition salt can be obtained, for example, by adding a neutralizing amount, or an excessive amount, of an acid to the free compound of formula (I) in a solvent such as water or methanol, and then subjecting the reaction mixture to concentration to dryness, lyophilization, or precipitation with a solvent such as ethanol or dioxane.

Examples of the acid used for this purpose are inorganic acids such as sulfuric acid, hydrochloric acid, hydrobromic acid, hydriodic acid, phosphoric acid, carbonic acid and nitric acid; and organic acids such as acetic acid, fumaric acid, malic acid, citric acid, mandelic acid, and succinic acid.

Separation and purification of the compound of formula (I) and its amino-protected product can be carried out by utilizing known techniques. It is especially preferred to use column chromatography. Cation exchange resins such as CM-Sephadex, Amberlite IRC-50, Amberlite IRC-84 and Amberlite CG-50 and carboxymethyl cellulose; silica gel, and cellulose are examples of adsorbents which can be utilized in performing column chromatography. The column can be developed with an alkaline aqueous solution such as aqueous ammonia or an aqueous solution of ammonium formate, or an organic solvent such as chloroform or methanol as a developing solvent by a concentration gradient method or a concentration stepwise method. Active fractions were collected from the eluates, and concentrated or lyophilized to obtain the desired compound in pure form.

Examples of the compound of formula (I) in accordance with this invention are shown below.

2'-N-(L-β-Lysyl)-KA-6606I and its acid addition salt;
2'-N-(L-β-Lysyl)-KA-6606II and its acid addition salt;
2'-N-(L-β-Lysyl)-KA-6606VI and its acid addition salt;
2'-N-(L-β-Lysyl)-KA-6606VIII and its acid addition salt;
2'-N-(L-β-Lysyl)-KA-6606XIV and its acid addition salt;
2'-N-(L-β-Lysyl)-KA-6606XIX and its acid addition salt;
2'-N-(L-β-Lysyl)-KA-7038I and its acid addition salt;
2'-N-(L-β-Lysyl)-KA-7038III and its acid addition salt;
2'-N-(L-β-Lysyl)-KA-7038VI and its acid addition salt;
2'-N-(L-β-Lysyl)-KA-7038IX and its acid addition salt;
2'-N-(L-β-Lysyl)-5-de-O-methyl-KA-6606I and its acid addition salt;

2'-N-(L-β-Lysyl)-5-de-O-methyl-KA-6606II and its acid addition salt;
2'-N-(L-β-Lysyl)-5-de-O-methyl-KA-6606VI and its acid addition salt;
2'-N-(L-β-Lysyl)-5-de-O-methyl-KA-6606VIII and its acid addition salt;
2'-N-(L-β-Lysyl)-5-de-O-methyl-KA-6606XIV and its acid addition salt;
2'-N-(L-β-Lysyl)-5-de-O-methyl-KA-6606XIX and its acid addition salt;
2'-N-(L-β-Lysyl)-5-de-O-methyl-KA-7038I and its acid addition salt;
2'-N-(L-β-Lysyl)-5-de-O-methyl-KA-7038III and its acid addition salt;
2'-N-(L-β-Lysyl)-5-de-O-methyl-KA-7038VI and its acid addition salt;
2'-N-(L-β-Lysyl)-5-de-O-methyl-KA-7038IX and its acid addition salt;
2'-N-(L-Lysyl)-KA-6606I and its acid addition salt;
2'-N-(L-Lysyl)-KA-6606II and its acid addition salt;
2'-N-(L-Lysyl)-KA-6606VI and its acid addition salt;
2'-N-(L-Lysyl)-KA-6606VIII and its acid addition salt;
2'-N-(L-Lysyl)-KA-6606XIV and its acid addition salt;
2'-N-(L-Lysyl)-KA-6606XIX and its acid addition salt;
2'-N-(L-Lysyl)-KA-7038I and its acid addition salt;
2'-N-(L-Lysyl)-KA-7038III and its acid addition salt;
2'-N-(L-Lysyl)-KA-7038VI and its acid addition salt;
2'-N-(L-Lysyl)-KA-7038IX and its acid addition salt;
2'-N-(L-Lysyl)-5-de-O-methyl-KA-6606I and its acid addition salt;
2'-N-(L-Lysyl)-5-de-O-methyl-KA-6606II and its acid addition salt;
2'-N-(L-Lysyl)-5-de-O-methyl-KA-6606VI and its acid addition salt;
2'-N-(L-Lysyl)-5-de-O-methyl-KA-6606VIII and its acid addition salt;
2'-N-(L-Lysyl)-5-de-O-methyl-KA-6606XIV and its acid addition salt;
2'-N-(L-Lysyl)-5-de-O-methyl-KA-6606XIX and its acid addition salt;
2'-N-(L-Lysyl)-5-de-O-methyl-KA-7038I and its acid addition salt;
2'-N-(L-Lysyl)-5-de-O-methyl-KA-7038III and its acid addition salt;
2'-N-(L-Lysyl)-5-de-O-methyl-KA-7038VI and its acid addition salt;
2'-N-(L-Lysyl)-5-de-O-methyl-KA-7038IX and its acid addition salt;

The compounds of formula (I) of this invention and their pharmaceutically acceptable acid addition salts exhibit superior antibiotic activity and are useful in the field of medicines for humans and animals, and also as intermediates for the synthesis of derivatives.

Thus, according to this invention, there can be provided an antibiotic composition comprising an antibiotically effective amount of the compound of formula (I) or a pharmaceutically acceptable acid addition salt thereof, and a pharmaceutically acceptable diluent or carrier.

The amount of the compound of formula (I) or its pharmaceutically acceptable acid addition salt is, for example, about 0.01 to about 99.5% by weight, based on the weight of the composition.

The antibiotic composition of this invention may be in any of the dosage forms usually employed, but injecting preparations and capsules are especially preferred. Preferably, like known water-soluble basic antibiotics, an injectable is prepared by filling a lyophilized powder of the antibiotic into a vial, preferably together with a stabilizer, and in use, the contents of the vial are dissolved in a dissolving liquid for administration.

The diluent or carrier includes, for example, liquid diluents such as distilled water for injection and physiological isotonic solution, and solid carriers such as lactose, starch, white sugar, glucose, crystalline cellulose, calcium carbonate, kaolin, D-mannitol, magnesium metasilicate aluminate, calcium sulfate, calcium phosphate and bentonite. Addition of stabilizers such as acidic sodium bisulfite is also preferred.

The dosage of the antibiotic substance of this invention can be suitably selected, and is, for example, about 0.01 to about 100 mg/kg/day.

Thus, according to this invention, there can be provided antibiotic compositions for animals other than human, such as poultry, domesticated animals and cultivated fish, and antibiotic compositions for human. These compositions are useful as antibacterial agents having a broad antibacterial spectrum.

The antibiotic activities (MIC) of some of the compounds of this invention are shown in Table 1 below in comparison with those of the starting compounds of formula (II).

TABLE 1

| Tested bacterium | MIC (μg/ml) | | | | | | |
|---|---|---|---|---|---|---|---|
| | KA-7038VI | 2'-N—β-Lysyl KA-7038VI | KA-6606 VIII | 2'-N—β-Lysyl KA-6606 VIII | 2'-N—β-Lysyl 5-de-O—Me KA-6606 VIII | KA-6606II | 2'-N—β-Lysyl 5-de-O—Me KA-6606II |
| S. aureus 209P JC-1 | 25 | 0.78 | 0.78 | 0.39 | 0.78 | 25 | 0.78 |
| S. faecalis Imanari | 100 | 1.56 | 3.13 | 1.56 | 3.13 | 100 | 3.13 |
| B. subtilis ATCC 6633 | 6.25 | 3.13 | 3.13 | 3.13 | 3.13 | 6.25 | 3.13 |
| E. coli NIHJ JC-2 | 50 | 1.56 | 3.13 | 1.56 | 6.25 | 50 | 3.13 |
| K. pneumoniae PCI 602 | 100 | 0.78 | 0.78 | 0.78 | 0.78 | >100 | 0.78 |
| E. cloacae IID 977 | >100 | 6.25 | 12.5 | 3.13 | 25 | >100 | 12.5 |
| S. marcescens NHL | >100 | 0.78 | 1.56 | 0.2 | 6.25 | 100 | 3.13 |
| P. inconstans 93 | >100 | 0.78 | 1.56 | 0.39 | 3.13 | >100 | 1.56 |
| P. vulgaris IID 874 | 50 | 25 | 12.5 | 12.5 | 100 | 100 | 25 |
| P. aeruginosa NCTC 10490 | >100 | 12.5 | 12.5 | 6.25 | 50 | >100 | 25 |
| P. cepacia IID 1340 | >100 | >100 | >100 | >100 | >100 | >100 | >100 |
| P. maltophilia IID 1275 | >100 | 1.56 | 1.56 | 1.56 | 1.56 | >100 | 1.56 |
| P. putida IID 5121 | >100 | 12.5 | 12.5 | 3.13 | 12.5 | >100 | 25 |
| E. coli ML 1410 | >100 | 1.56 | 3.13 | 0.78 | 6.25 | >100 | 6.25 |
| E. coli ML 1410 R81 (APH(3')-I) | >100 | 1.56 | 3.13 | 0.78 | 6.25 | >100 | 6.25 |

TABLE 1-continued

| | MIC (μg/ml) | | | | | | |
|---|---|---|---|---|---|---|---|
| Tested bacterium | KA-7038VI | 2'-N—β-Lysyl KA-7038VI | KA-6606 VIII | 2'-N—β-Lysyl KA-6606 VIII | 2'-N—β-Lysyl 5-de-O—Me KA-6606 VIII | KA-6606II | 2'-N—β-Lysyl 5-de-O—Me KA-6606II |
| P. aeruginosa TI 13 (APH(3')-I) | 100 | 25 | 25 | 25 | 50 | >100 | 50 |
| E. coli ML 1410 R83 (APH(3')-II) | >100 | 3.13 | 6.25 | 0.78 | 6.25 | >100 | 6.25 |
| P. aerugionosa TK-157 (APH(3')-II) | >100 | 25 | 25 | 25 | 50 | >100 | 50 |
| E. coli ML 1410 R102 (AAD(2")) | 100 | 3.13 | 0.78 | 0.39 | 1.56 | >100 | 12.5 |
| K. pneumoniae 4687 (AAD(2")) | >100 | 3.13 | 6.25 | 0.78 | 12.5 | >100 | 12.5 |
| E. coli ML 1410 R82 (AAD(3")) | >100 | 3.13 | 3.13 | 0.39 | 6.25 | >100 | 6.25 |
| P. aeruginosa GN315 (AAC(6')-IV) | >100 | 100 | 100 | 25 | >100 | >100 | >100 |
| E. coli JR 88 (AAC(3)-I) | >100 | 3.13 | 50 | 0.78 | 6.25 | >100 | 12.5 |
| P. aeruginosa 99 (AAC(3)-I) | >100 | >100 | >100 | 50 | >100 | >100 | >100 |
| E. coli R176 (AAC(3)-II) | >100 | 1.56 | 3.13 | 0.78 | 6.25 | >100 | 6.25 |
| P. aeruginosa RST-1 (AAC(3)-III) | >100 | >100 | 100 | 100 | >100 | >100 | 100 |
| P. inconstans GN1554 (AAC(2')) | >100 | 0.78 | 1.56 | 0.2 | 1.56 | >100 | 1.56 |

The following Examples specifically illustrate the compounds of this invention and their acid addition salts and the production of these compounds.

EXAMPLE 1

Production of 2'-N-(L-β-lysyl)-KA-7038VI:

(A) Seventy-two milligrams of KA-7038VI was dissolve in 22 ml of methanol, and 86 mg of nickel acetate tetrahydrate was added. The mixture was stirred at room temperature for 1 hour, and cooled with ice. Then, 96 mg of an N-hydroxysuccinimide ester of bis-N-benzyloxycarbonyl-L-β-lysine was added, and the mixture was stirred overnight. Concentrated aqueous ammonia (0.6 ml) was added to the reaction mixture, and the mixture was stirred for one hour, followed by concentration to dryness. The residue was dissolved in 20 ml of chloroform and 20 ml of water, and the aqueous layer was separated. The aqueous layer was diluted to a volume of 50 ml, and adsorbed onto a column of Amberlite CG-50 (NH4+ form). The column was eluted with 1N aqueous ammonia. The eluate was concentrated to dryness, and adsorbed onto a column of CM-Sephadex C-25 (NH4+ form). The column was eluted by a concentration gradient method between water and 0.3N aqueous ammonia. Fractions containing the desired product were collected and concentrated to dryness to give 7.4 mg of 2'-N-(bis-N-benzyloxycarbonyl-L-β-lysyl)-KA-7038VI as a colorless powder.

Specific rotation: $[\alpha]_D^{21} + 54°$ (c 0.36, H2O)
$^1$H-NMR: $\delta_{0.1N\,NaOD, ppm}^{TMS}$
2.31 (3H, s, N—CH3),
2.43 (3H, s, N—C$\underline{H}$3),
3.37 (3H, s, O—C$\underline{H}$3),
5.10 (4H, s,

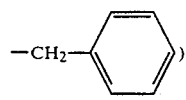
)

7.42 (10H, s, aromatic ring H).

| Elemental analysis for C37H56N6O9: | | | |
|---|---|---|---|
| | C | H | N |
| Calculated (%) | 60.97 | 7.74 | 11.53 |
| Found (%) | 60.64 | 7.62 | 11.27 |

(B) The N-protected compound obtained in (A) (7.4 mg) was dissolved in 0.46 ml of 0.2N methanolic hydrogen chloride, and 8 mg of 5% palladium-on-carbon was added to perform catalytic reduction at room temperature under atmospheric pressure. The catalyst was removed by filtration from the reaction mixture. The filtrate was concentrated to dryness under reduced pressure, and the residue was adsorbed onto a column of CM-Sephadex C-25. The column was eluted with 1N aqueous ammonia. Fractions containing the desired product were collected and lyophilized to give 4.0 mg of 2'-N-(L-β-lysyl)-KA-7038VI of the following structural formula as a colorless solid.

Specific rotation: $[\alpha]_D^{21} + 57°$ (c 0.4, H2O)
$^1$H—NMR: $\delta D_2O,^{TMS}$ ppm.
2.24 (1H, dd, J=8.0, 13.5 Hz, $$-NH-CO-\underset{H}{\overset{H}{\underset{|}{C}}}-)$$

2.39 (1H, dd, J=4.9, 13.5 Hz, $$-NH-CO-\underset{H}{\overset{H}{\underset{|}{C}}}-)$$

2.41 (3H, s, N—CH3),
2.46 (3H, s, N—C$\underline{H}$3),
3.39 (3H, s, O—C$\underline{H}$3),
5.09 (1H, d, J=3.6 Hz, H—1')

| Elemental analysis for C21H44N6O5.H2O: | | | |
|---|---|---|---|
| | C | H | N |
| Calculated (%) | 52.70 | 9.69 | 17.56 |

-continued

| Elemental analysis for $C_{21}H_{44}N_6O_5 \cdot H_2O$: | | | |
|---|---|---|---|
| | C | H | N |
| Found (%) | 52.31 | 9.70 | 17.42 |

Four milligrams of 2'-N-(L-β-lysyl)-KA-7038VI prepared as above was dissolved in 2 ml of water, and dilute sulfuric acid was added to adjust the solution to pH 6.0. The solution was lyophilized to give 2'-N-(L-β-lysyl)-KA-7038VI.hexasulfate as a powder.

By a similar operation, the following acid addition salts were obtained from the corresponding acids.

Hydrochloride, hydrobromide, hydriodide, phosphate, carbonate, nitrate, acetate, fumarate, malate, citrate, mandelate, and succinate.

The above procedure of Example 1 was repeated except that KA-7038III, 5-de-O-methyl-KA-7038III, and 5-de-O-methyl-KA-7038VI were used instead of KA-7038VI. The following compounds were obtained.

2'-N-(L-β-lysyl)-KA-7038III and its acid addition salts;

2'-N-(L-β-lysyl)-5-de-O-methyl-KA-7038III and its acid addition salts; and 2'-N-(L-β-lysyl)-5-de-O-methyl-KA-7038VI and its acid addition salts.

EXAMPLE 2

Production of 2'-N-(L-β-lysyl)-KA-6606VIII:

(A) Thirty-two milligrams of KA-6606VIII was dissolved in 1.0 ml of methanol, and 42 mg of nickel acetate tetrahydrate was added. The mixture was stirred at room temperature for 1 hour, and then cooled with ice. Then, 44.6 mg of an N-hydroxysuccinimide ester of bis-N-benzyloxycarbonyl-L-β-lysine was added, and the mixture was stirred overnight. Hydrogen sulfide gas was blown into the reaction mixture, and the resulting precipitate was removed by filtration. The filtrate was concentrated to dryness. The residue was dissolved in 30 ml of chloroform and 30 ml of water, and the aqueous layer was separated. The aqueous layer was passed through a column of Amberlite CG-50 (NH$_4$+ form), and the column was eluted with 1N aqueous ammonia. The eluate was concentrated to dryness, and adsorbed onto CM-Sephadex C-25 (NH$_4$+ form). The column was eluted by a concentration gradient method between water and 0.3N aqueous ammonia. Fractions containing the desired product were collected and concentrated to dryness. The residue was purified by preparative thin-layer chromatography [Silica Gel PF$_{254}$ (a product of Merck & Co.); developing solvent, the lower layer of chloroform/methanol/17% aqueous ammonia (2/1/1)] to give 9 mg of 2'-N-(bis-N-benzyloxycarbonyl-L-β-lysyl)-KA-6606VIII.

Specific rotation: $[\alpha]_D^{20} + 44°$ (c 0.41, H$_2$O)
$^1$H—NMR: δD$_2$O,$^{TMS}$ ppm,
1.14 (3H, d, J=6.8 Hz, C—CH$_3$),
2.44 (3H, s, N—CH$_3$),
3.37 (3H, s, O—CH$_3$),
4.98 (1H, d, J=4.0 Hz, H—1'),
5.10 (4H, s,

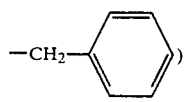

)

7.40 (10H, s, aromatic ring H)

| Elemental analysis for $C_{37}H_{56}N_6O_9$ | | | |
|---|---|---|---|
| | C | H | N |
| Calculated (%) | 60.97 | 7.74 | 11.53 |
| Found (%) | 60.49 | 7.41 | 11.34 |

(B) The N-protected compound obtained in (A) (9.6 mg) was dissolved in 0.78 ml of 0.2N methanolic hydrogen chloride. Ten milligrams of 5% palladium-on-carbon was added to perform catalytic reduction at room temperature under atmospheric pressure. The catalyst was removed by filtration, and the filtrate was concentrated to dryness under reduced pressure. The residue was adsorbed onto a column of CM-Sephadex, and the column was eluted with 1N aqueous ammonia. Fractions containing the desired product were collected and lyophilized to give 5 mg of 2'-N-(L-β-lysyl)-KA-6606VIII of the following structural formula as a colorless solid.

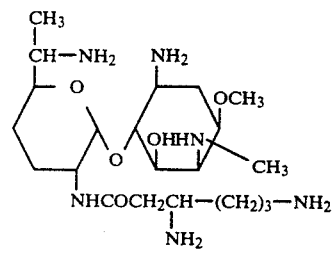

Specific rotation: $[\alpha]_D^{21} + 70°$ (c 0.23, H$_2$O)
$^1$H—NMR: δ2.8N ND$_4$OD, ppm$^{TMS}$,
1.03 (3H, d, J=6.5 Hz, C—CH$_3$)
2.20 (1H, dd, J=8.0, 14.0 Hz,

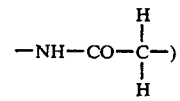

2.36 (1H, dd, J=5.8, 14.0 Hz,

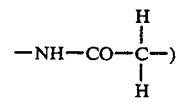

2.47 (3H, s, N—CH$_3$)
3.38 (3H, s, O—CH$_3$)
5.06 (1H, d, J=3.6 Hz, H—1')

| Elemental analysis for: $C_{21}H_{44}N_6O_5 \cdot 2H_2O$: | | | |
|---|---|---|---|
| | C | H | N |
| Calculated (%) | 50.79 | 9.74 | 16.92 |
| Found (%) | 51.07 | 9.50 | 17.11 |

(C) The product obtained in (B) above was treated in the same way as in Example 1, (C) to give the following acid addition salts.

Sulfate, hydrochloride, hydrobromide, hydriodide, phosphate, carbonate, nitrate, acetate, fumarate, malate, citrate, mandelate, and succinate.

Example 2 was repeated except that KA-6606VI was used instead of KA-6606VIII. There was obtained 2'-N-(L-β-lysyl)-KA-6606VI and its acid addition salts.

EXAMPLE 3

Production of 2'-N-(L-β-lysyl)-5-de-O-methyl-KA-6606VIII:

(A) Fifteen milligrams of 5-de-O-methyl-KA-6606VIII was dissolved in 0.6 ml of methanol, and 21 mg of an N-hydroxysuccinimide ester of bis-N-benzyloxy-carbonyl-L-β-lysine was added under ice cooling. The mixture was stirred overnight. To the reaction mixture was added 20 mg of benzyloxycarbonyloxy succinimide, and the mixture was left to stand at room temperature for 3 hours. The reaction mixture was concentrated to dryness, and the residue was dissolved in chloroform, washed with water and then dried. The solvent was evaporated, and the residue was purified by preparative thin-layer chromatography [Silica Gel PF$_{254}$; solvent, chloroform-methanol (10:1)] to give 10 mg of 1,4,6'-tris-N-benzyloxycarbonyl-2'-N-(bis-N-benzyloxycarbonyl-L-β-lysly)-5-de-O-methyl-KA-6606VIII as white solid.

Specific rotation: $[\alpha]_D^{23} +40°$ (c 0.5, CHCl$_3$)
$^1$H—NMR: δCDCL$_3$, ppm
3.28 (3H, s, N—C$\underline{H}_3$)

| Elemental analysis for C$_{60}$H$_{72}$N$_6$O$_{15}$: | | | |
|---|---|---|---|
| | C | H | N |
| Calculated (%) | 64.50 | 6.50 | 7.52 |
| Found (%) | 64.04 | 6.66 | 7.28 |

(B) Nine milligrams of the N-protected compound obtained in (A) was dissolved in 0.54 ml of 0.2N methanolic hydrogen chloride, catalytically reduced, treated and purified in the same way as in Example 2, (B) to give 3 mg of 2'-N-(L-β-lysyl)-5-de-O-methyl-KA-6606VIII having the following structural formula as a colorless solid.

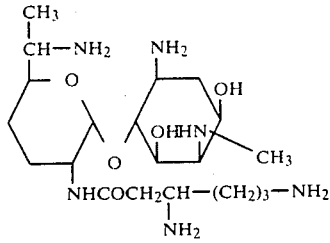

Specific rotation: $[\alpha]_D^{22} +76°$ (c 0.2, H$_2$O)
$^1$H—NMR: δD$_2$O, ppm$^{TMS}$
1.04 (3H, d, J=6.7 Hz, C—C$\underline{H}_3$),
2.21 (1H, dd, J=8, 14 Hz,

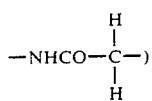

2.37 (1 H, dd, J=5.5, 14 Hz,

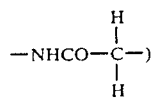

2.48 (3H, s, N—C$\underline{H}_3$)
2.64 (2H, t, J=6.5 Hz,

—C$\underline{H}$—CH$_2$—CH$_2$—CH$_2$—NH$_2$)
|
NH$_2$ 5.08 (1H, d, J=3.5 Hz, H—1')

| Elemental analysis for C$_{20}$H$_{42}$N$_6$O$_5$.H$_2$O: | | | |
|---|---|---|---|
| | C | H | N |
| Calculated (%) | 51.93 | 9.15 | 18.17 |
| Found (%) | 51.44 | 9.01 | 17.59 |

(C) The product obtained in (B) above was treated in the same way as in Example 1, (C) to give the following acid addition salts.

Sulfate, hydrochloride, hydrobromide, hydriodide, phosphate, carbonate, nitrate, acetate, fumarate, malate, citrate, mandelate and succinate.

Example 3 was repeated except that 5-de-O-methyl-KA-6606VI was used instead of 5-de-O-methyl-KA-6606VIII. There were obtained 2'-N-(L-β-lysyl)-5-de-O-methyl-KA-6606VI and its acid addition salts.

EXAMPLE 4

Production of 2'-N-(L-β-lysyl)-5-de-O-methyl-KA-6606I:

(A) 5-De-O-methyl-KA-6606II (6.3 g) was dissolved in 200 ml of methanol, and 15 g of nickel acetate tetrahydrate was added. The mixture was stirred at room temperature for 30 minutes, and 7.9 g of S-p-methoxybenzyloxycarbonyl-4,6-dimethyl-2-mercaptopyrimidine was added. The mixture was stirred overnight. Concentrated aqueous ammonia (70 ml) was added to the reaction mixture, and the mixture was stirred for 1 hour and concentrated to dryness. The residue was dissolved in 250 ml of chloroform and 250 ml of water. The insoluble materials were removed by filtration, and the aqueous layer was separated. The chloroform layer was extracted further with water, and the extract was combined with the previous aqueous layer. The combined layers were concentrated to dryness. The residue was chromatographed on a column of silica gel, and the column was eluted with the lower layer of chloroform/methanol/17% aqueous ammonia (2:1:1). Fractions containing the desired product were collected and concentrated to dryness to give 2.4 g of 5-de-O-methyl-2'-N-(p-methoxy-benzyloxycarbonyl)-KA-6606II as a colorless solid.

Specific rotation: $[\alpha]_D^{23} +134°$ (c 1, H$_2$O)
$^1$H—NMR: δD$_2$O, ppm$^{TMS}$,
1.44 (3H, d, J=6.5 Hz, C—C$\underline{H}_3$ )
2.63 (3H, s, N—C$\underline{H}_3$),
4.17 (3H, s,

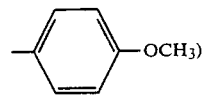

| Elemental analysis for C$_{23}$H$_{38}$N$_4$O$_7$: | | | |
|---|---|---|---|
| | C | H | N |
| Calculated (%) | 57.24 | 7.94 | 11.61 |
| Found (%) | 57.01 | 7.66 | 11.35 |

(B) One hundred and seventeen milligrams of the 2'-N-protected compound obtained in (A) was dissolved in 3.5 ml of methanol, and 181 mg of nickel acetate tetrahydrate was added. The mixture was stirred at room temperature for 1 hour, and then 133 mg of benzyloxycarbonyloxy succinimide was added. The mixture was stirred for 1 hour.

To the reaction mixture was added 3.5 ml of a 30% ethanol solution of methylamine, and the mixture was stirred for 1 hour and then concentrated to dryness. The residue was dissolved in 20 ml of chloroform, and washed with 3N aqueous ammonia and then with water. The solvent was then evaporated.

The residue was dissolved in 5.8 ml of dioxane, and 150 mg of an N-hydroxysuccinimide ester of N-benzyloxycarbonylglycine and 0.38 ml of triethylamine were added. The mixture was warmed at 37° C. overnight.

The solvent was evaporated. The residue was dissolved in 20 ml of chloroform, washed with water, dried, and then concentrated to dryness. The residue was dissolved in 6 ml of methanol, and 1 ml of concentrated aqueous ammonia was added. The mixture was left to stand at room temperature for 1 hour. The solvent was evaporated, and the residue was purified by silica gel column chromatography [carrier, Wako Gel C-200; solvent, chloroform-methanol (195:5)] to give 142 mg of 1,6'-bis-N-benzyloxycarbonyl-4-N-(N-benzyloxycarbonylglycyl)-5-de-O-methyl-2'-N-(p-methoxybenzyloxycarbonyl)-KA-6606II as a colorless solid.

Specific rotation: $[\alpha]_D^{20} + 38°$ (c 2, CHCl$_3$)
IR: $\nu_{max}^{CHCl_3}$, cm$^{-1}$
1640 (amide I)
$^1$H—NMR: $\delta_{CDCl_3}^{TMS}$, ppm,
1.01 (3H, d, J=6.5 Hz, C—CH$_3$),
2.90 (3H, s, N—CH$_3$),
3.68 (3H, s,

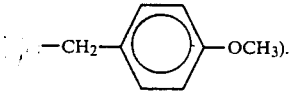

).

| Elemental analysis for C$_{49}$H$_{59}$N$_5$O$_{14}$: | | | |
|---|---|---|---|
| | C | H | N |
| Calculated (%): | 62.47 | 6.31 | 7.43 |
| Found (%): | 62.05 | 6.18 | 7.25 |

(C) Sixty four milligrams of the 4-N-glycyl compound obtained in (B) above was dissolved in 1 ml of a 0.5N acetic acid solution of p-toluenesulfonic acid, and 40 mg of anisole was added. The mixture was stirred room temperature for 3 hours.

The solvent was evaporated from the reaction mixture. The residue was dissolved in 20 ml of chloroform, and washed with a 1N aqueous solution of sodium hydroxide and then with water, and thereafter dried. The solvent was evaporated.

The residue was dissolved in 0.8 ml of dioxane, and 26 mg of an N-hydroxysuccinimide ester of bis-N-benzyloxycarbonyl-L-β-lysine and 0.05 ml of triethylamine were added. The mixture was stirred overnight at room temperature.

The solvent was evaporated, and the residue was dissolved in chloroform, washed with water, and dried. The solvent was evaporated. The residue was purified by preparative thin-layer chromatography [carrier, Silica Gel 60PF$_{254}$ (a product of Merck & Co.); developing solvent, chloroform-methanol (10:1)] to give 27 mg of 1,6'-bis-N-benzyloxycarbonyl-4-N-(N-benzyloxycarbonyl-glycyl)-2'-N-(bis-N-benzyloxycarbonyl-L-β-lysyl)-5-de-O-methyl-KA-6606II as a colorless solid.

Specific rotation: $[\alpha]_D^{23} + 53°$ (c 1, CHCl$_3$)
IR: $\nu_{max}^{CHCl_3}$, cm$^{-1}$,
1628 (amide I)
$^1$H—NMR: $\delta_{CDCl_3}^{TMS}$, ppm,
1.02 (3H, d, J=7.0 Hz, C—CH$_3$),
3.07 (3H, s, N—CH$_3$).

| Elemental analysis for C$_{62}$H$_{75}$N$_7$O$_{16}$: | | | |
|---|---|---|---|
| | C | H | N |
| Calculated (%) | 63.41 | 6.44 | 8.35 |
| Found (%) | 63.48 | 6.31 | 8.08 |

(D) Twenty seven milligrams of the N-protected compound obtained in (C) was dissolved in 0.2N methanolic hydrogen chloride, and 30 mg of 5% palladium-on-carbon was added to perform catalytic reduction at room temperature under atmospheric pressure.

The catalyst was removed from the reaction mixture by filtration. The filtrate was concentrated to dryness and lyophilized to give 15 mg of 2'-N-(L-β-lysyl)-5-de-O-methyl-KA-6606I hydrochloride having the following structural formula.

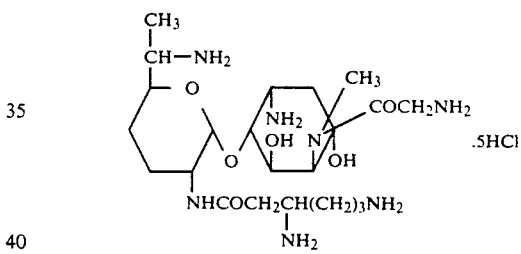

Specific rotation: $[\alpha]_D^{23} + 87°$ (c 0.75, H$_2$O)
$^1$H—NMR: $\delta_{D_2O}^{TMS}$, ppm,
1.34 (3H, d, J=7.0 Hz, C—CH$_3$),
3.11 (3H, s, N—CH$_3$),
5.25 (1H, d, J=3.5 Hz, H—1').

| Elemental analysis for C$_{22}$H$_{45}$N$_7$O$_6$.5HCl.2H$_2$O | | | | |
|---|---|---|---|---|
| | C | H | N | Cl |
| Calculated (%): | 36.60 | 7.54 | 13.58 | 24.55 |
| Found (%): | 36.22 | 7.66 | 13.31 | 24.72 |

The following compounds were obtained by repeating Example 4 except that KA-6606II, KA-7038III and 5-de-O-methyl-KA-7038III were used instead of 5-demethyl-KA-6606II.

2'-N-(L-β-lysyl)-KA-6606I and its acid addition salts;
2'-N-(L-β-lysyl)-KA-7038I and its acid addition salts;
and 2'-N-(L-β-lysyl)-5-de-O-methyl-KA-7038I and its acid addition salts.

EXAMPLE 5

Production of 2'-N-(L-β-lysyl)-5-de-O-methyl-KA-6606II:

(A) Two hundred milligrams of 5-de-O-methyl-2'-N-(p-methoxybenzyloxycarbonyl)-KA-6606II obtained in Example 4, (A) was dissolved in 6 ml of methanol, and 400 mg of benzyloxycarbonyloxy succinimide and 50 mg of triethylamine were added. The mixture was stirred overnight at room temperature.

Concentrated aqueous ammonia (1 ml) was added to the reaction mixture, and the mixture was stirred for 1 hour and then concentrated to dryness. The residue was dissolved in 20 ml of chloroform, washed with water and dried. The solvent was evaporated. The residue was purified by silica gel column chromatography [solvent, chloroform-methanol (97:3)] to give 118 mg of 1,4,6'-tris-N-benzyloxycarbonyl-5-de-O-methyl-2'-N-(p-methoxybenzyloxycarbonyl)-KA-6606II as a colorless solid.

Specific rotation: $[\alpha]_D^{20} + 39°$ (c 2, CHCl$_3$),
$^1$H—NMR: $\delta_{CDCL_3}^{TMS}$, ppm,
1.04 (3H, d, J=6.5 Hz, C—C$\underline{H}_3$),
3.00 (3H, s, N—C$\underline{H}_3$),
3.65 (3H, s,

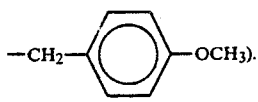

).

| Elemental analysis for C$_{47}$H$_{56}$N$_4$O$_{13}$: | | | |
|---|---|---|---|
| | C | H | N |
| Calculated (%): | 63.79 | 6.38 | 6.33 |
| Found (%): | 63.57 | 6.44 | 6.21 |

(B) The 2'-N-protected compound obtained in (A) (118 mg) above was dissolved in 1.9 ml of a 0.5N acetic acid solution of p-toluenesulfonic acid, and 73 mg of anisole was added. The mixture was stirred at room temperature for 3 hours.

The solvent was evaporated. The residue was dissolved in 15 ml of chloroform, washed with a 1N aqueous solution of sodium hydroxide and water, and dried. The solvent was evaporated. The residue was purified by preparative thin-layer chromatography [carrier, Silica Gel PF$_{254}$ (a product of Merck & Co.); developing solvent, chloroform/methanol/concentrated aqueous ammonia (6:1:0.1)] to give 57 mg of 1,4,6'-tris-N-benzyloxycarbonyl-5-de-O-methyl-KA-6606II as a solid.

(C) Fifty seven milligrams of the 1,4,6'-tris-N-protected compound obtained in (B) was dissolved in 1.7 ml of dioxane, and 60 mg of an N-hydroxysuccinimide ester of bis-N-benzyloxycarbonyl-L-β-lysine and 0.1 ml of triethylamine was added. The mixture was stirred at room temperature for 6 hours.

The solvent was evaporated. The residue was dissolved in 8 ml of chloroform, washed with water and then dried. The solvent was evaporated. The residue was purified by preparative thin-layer chromatography [carrier, Silica Gel PF$_{254}$ (a product of Merck & Co.); developing solvent, chloroform-methanol (15:1)] to give 53 mg of 1,4,6'-tris-N-benzyloxycarbonyl-2'-N-(bis-N-benzyloxycarbonyl-L-β-lysyl)-5-de-O-methyl-KA-6606II as a colorless solid.

Specific rotation: $[\alpha]_D^{19} + 52°$ (c 1, CHCl$_3$)
IR: $\nu_{max}^{CHCl_3}$, cm$^{-1}$,
1650 (amide I)
$^1$H—NMR: $\delta_{CDCl_3}^{TMS}$, ppm,
1.01 (3H, br. d, C—C$\underline{H}_3$),
3.12 (3H, s, N—C$\underline{H}_3$).

| Elemental analysis for C$_{60}$H$_{72}$N$_6$O$_{15}$ | | | |
|---|---|---|---|
| Calculated (%): | 64.50 | 6.50 | 7.52 |
| Found (%): | 64.70 | 6.54 | 7.27 |

(D) Fifty three milligrams of the N-protected compound obtained in (C) above was dissolved in 2 ml of acetic acid, and 53 mg of 5% palladium-on-carbon was added to perform catalytic reduction at room temperature under atmospheric pressure. The catalyst was removed from the reaction mixture by filtration. The filtrate was diluted with 200 ml of water, and neutralized with concentrated aqueous ammonia. The neutralized solution was charged on a column (1×20 cm) of CM-Sephadex C-25 (NH$_4^+$ form). The column was washed with water, and then developed by a concentration gradient method between 0.7N aqueous ammonia and 1.0N aqueous ammonia. Fractions containing the desired product were collected, concentrated, and lyophilized to give 4.8 mg of 2'-N-(L-β-lysyl)-5-de-O-methyl-KA-6606II having the following structural formula.

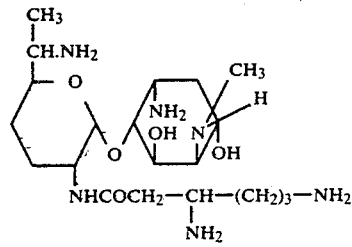

Specific rotation: $[\alpha]_D^{19} + 133°$ (c 0.15, H$_2$O)
$^1$H—NMR: $\delta_{0.1N\ NaOD}^{TMS\ (internal\ standard)}$, ppm,
1.04 (3H, d, J=7.5 Hz, C—C$\underline{H}_3$),
2.30 (3H, s, N—C$\underline{H}_3$),
5.07 (1H, br. d, H—1').

| Elemental analysis for C$_{20}$H$_{42}$N$_6$O$_5$·H$_2$O: | | | |
|---|---|---|---|
| | C | H | N |
| Calculated (%): | 51.70 | 9.55 | 18.09 |
| Found (%): | 52.03 | 9.82 | 17.80 |

The following compounds were obtained by repeating Example 5, (C) and (D) except that tris-N-protected compounds of KA-6606II, KA-6606XIV, KA-6606XIX, KA-7038IX, 5-de-O-methyl-KA-6606XIV, 5-de-O-methyl-KA-6606XIX and 5-de-O-methyl-KA-7038IX were used as starting materials instead of the tris-N-protected-5-de-O-methyl-KA-6606II.

2'-N-(L-β-lysyl)-KA-6606II and its acid addition salts;

2'-N-(L-β-lysyl)-KA-6606XIV and its acid addition salts;

2'-N-(L-β-lysyl)-KA-6606XIX and its acid addition salts;

2'-N-(L-β-lysyl)-KA-7038IX and its acid addition salts;

2'-N-(L-β-lysyl)-5-de-O-methyl-KA-6606XIV and its acid addition salts;

2'-N-(L-β-lysyl)-5-de-O-methyl-KA-6606XIX and its acid addition salts; and

2'-N-(L-β-lysyl)-5-de-O-methyl-KA-7038IX and its acid addition salts.

EXAMPLE 6

Production of 2'-N-(L-lysyl)-5-de-O-methyl-KA-6606I:

(A) 1,6'-bis-N-benzyloxycarbonyl-4-N-(N-benzyloxycarbonylglycyl)-5-de-O-methyl-2'-N-(p-methoxybenzyloxycarbonyl)-KA-6606II (112 mg) obtained in Example 4, (B) was dissolved in 1.7 ml of a 0.5N acetic acid solution of p-toluenesulfonic acid, and 69 mg of anisole was added. The mixture was stirred at room temperature for 3 hours.

The solvent was evaporated. The residue was dissolved in 15 ml of chloroform, washed with a 1N aqueous solution of sodium hydroxide and then with water, dried and the solvent was evaporated. The residue was purified by preparative thin-layer chromatography [carrier, Silica Gel 60PF$_{254}$ (a product of Merck & Co.); developing solvent, chloroform/methanol/concentrated aqueous ammonia (6:1:0.1)] to give 36 mg of a solid.

The resulting solid was dissolved in 2 ml of dioxane, and 40 mg of an N-hydroxysuccinimide ester of bis-N-benzyloxycarbonyl-L-α-lysine and 0.08 ml of triethylamine were added. The mixture was left to stand at room temperature overnight. The solvent was evaporated. The residue was dissolved in 8 ml of chloroform, washed with water and dried. The solvent was evaporated, and the residue was purified by preparative thin-layer chromatography [carrier, Silica Gel 60PF$_{254}$ (a product of Merck & Co.); developing solvent, chloroform-methanol (15:1)] to give 33 mg of 1,6'-bis-N-benzyloxycarbonyl-4-N-(N-benzyloxycarbonylglycyl)-2'-N-(bis-N-benzyloxycarbonyl-L-lysyl)-5-de-O-methyl-KA-6606II as a colorless solid.

Specific rotation: $[\alpha]_D^{28} + 41°$ (c 1, CHCl$_3$)
IR: $\nu_{max}^{CHCl_3}$, cm$^{-1}$,
1635 (amide I)
$^1$H—NMR: $\delta_{CDCl_3}^{TMS}$, ppm,
1.00 (3H, m, C—C$\underline{H}_3$),
3.05 (3H, s, N—C$\underline{H}_3$).

| Elemental analysis for C$_{62}$H$_{75}$N$_7$O$_{16}$: | | | |
|---|---|---|---|
| | C | H | N |
| Calculated (%): | 63.41 | 6.44 | 8.35 |
| Found (%): | 63.60 | 6.64 | 8.11 |

(B) Thirty three milligrams of the N-protected compound obtained in (A) above was dissolved in 1.7 ml of 0.2N methanolic hydrogen chloride, and 34 mg of 5% palladium-on-carbon was added to perform catalytic reduction at room temperature under atmospheric pressure.

The catalyst was removed from the reaction mixture by filtration. The filtrate was concentrated to dryness, and lyophilized to give 20 mg of 2'-N-(L-lysyl)-5-de-O-methyl-KA-6606I hydrochloride having the following structural formula as a colorless powder.

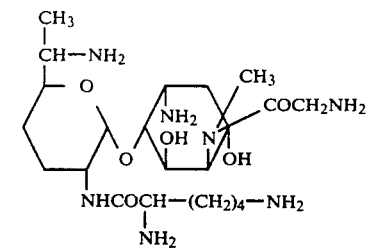

Specific rotation: $[\alpha]_D^{27} + 86°$ (c 1, H$_2$O)
$^1$H—NMR: $\delta_{D_2O}^{TMS}$, ppm,
1.34 (3H, d, J=7.0 Hz, C—C$\underline{H}_3$),
3.11 (3H, s, N—C$\underline{H}_3$),
5.19 (1H, d, J=3.5 Hz, H—1').

| Elemental analysis for C$_{22}$H$_{45}$N$_7$O$_6$.5HCl.2H$_2$O: | | | |
|---|---|---|---|
| | C | H | N | Cl |
| Calculated (%): | 36.60 | 7.54 | 13.58 | 24.55 |
| Found (%): | 36.43 | 7.74 | 13.29 | 24.84 |

When the same N-protected-lysine as used in Example 6 was used instead of the N-protected β-lysines in Examples 1 to 5, the following compounds were obtained.

2'-N-(L-lysyl)-KA-6606I and its acid addition salts;
2'-N-(L-lysyl)-KA-6606II and its acid addition salts;
2'-N-(L-lysyl)-KA-6606VI and its acid addition salts;
2'-N-(L-lysyl)-KA-6606VIII and its acid addition salts;
2'-N-(L-lysyl)-KA-6606XIV and its acid addition salts;
2'-N-(L-lysyl)-KA-6606XIX and its acid addition salts;
2'-N-(L-lysyl)-KA-7038I and its acid addition salts;
2'-N-(L-lysyl)-KA-7038III and its addition salts;
2'-N-(L-lysyl)-KA-7038VI and its acid addition salts;
2'-N-(L-lysyl)-KA-7038IX and its acid addition salts;
2'-N-(L-lysyl)-5-de-O-methyl-KA-6606II and its acid addition salts;
2'-N-(L-lysyl)-5-de-O-methyl-KA-6606VI and its acid addition salts;
2'-N-(L-lysyl)-5-de-O-methyl-KA-6606VIII and its acid addition salts;
2'-N-(L-lysyl)-5-de-O-methyl-KA-6606XIV and its acid addition salts;
2'-N-(L-lysyl)-5-de-O-methyl-KA-6606XIX and its acid addition salts;
2'-N-(L-lysyl)-5-de-O-methyl-KA-7038I and its acid addition salts;
2'-N-(L-lysyl)-5-de-O-methyl-KA-7038III and its acid additions salts;
2'-N-(L-lysyl)-5-de-O-methyl-KA-7038VI and its acid additions salts; and
2'-N-(L-lysyl)-5-de-O-methyl-KA-7038IX and its acid addition salts.

What is claimed is:
1. A compound of the formula

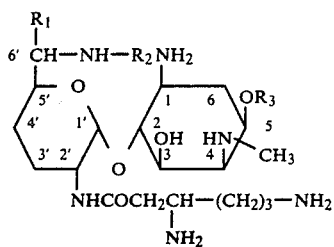

wherein each of $R_1$, $R_2$ and $R_3$ represents H or $CH_3$, provided that $R_1$ and $R_2$ are not $CH_3$ at the same time, or an acid addition salt thereof.

2. The compound and the acid addition salt thereof according to claim 1 wherein said compound is 2'-N-(L-β-lysyl)-KA-7038VI.

3. The compound and the acid addition salt thereof according to claim 1 wherein said compound is 2'-N-(L-β-lysyl)-KA-6606VIII.

4. The compound and the acid addition salt thereof according to claim 1 wherein said compound is 2'-N-(L-β-lysyl)-5-de-O-methyl-KA-6606VIII.

* * * * *